US008398597B2

(12) United States Patent
Brimhall

(10) Patent No.: US 8,398,597 B2
(45) Date of Patent: Mar. 19, 2013

(54) NEEDLE SHIELD AND INTERLOCK

(75) Inventor: Greg L. Brimhall, West Jordan, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 281 days.

(21) Appl. No.: 12/140,675

(22) Filed: Jun. 17, 2008

(65) Prior Publication Data

US 2009/0312711 A1  Dec. 17, 2009

(51) Int. Cl.
*A61M 5/178* (2006.01)

(52) U.S. Cl. .................................. 604/164.08

(58) Field of Classification Search .......... 604/158–163, 604/164.01–164.09, 168.01, 166.01, 164.1, 604/164.11–164.13, 165.01–165.04, 272
See application file for complete search history.

(56) References Cited

U.S. PATENT DOCUMENTS

| 5,135,504 | A | 8/1992 | McLees |
| 5,215,525 | A | 6/1993 | Sturman |
| 5,458,658 | A | 10/1995 | Sircom |
| 5,599,310 | A | 2/1997 | Bogert |
| 5,772,636 | A | 6/1998 | Brimhall et al. |
| 5,792,122 | A | 8/1998 | Brimhall et al. |
| 5,830,189 | A | 11/1998 | Chang |
| 6,010,487 | A | 1/2000 | DeMichele et al. |
| 6,221,047 | B1 | 4/2001 | Greene et al. |
| 6,287,278 | B1 | 9/2001 | Woehr et al. |
| 6,595,954 | B1 * | 7/2003 | Luther et al. .................. 604/110 |
| 6,616,630 | B1 * | 9/2003 | Woehr et al. .................. 604/110 |
| 6,652,486 | B2 | 11/2003 | Bialecki et al. |
| 6,663,592 | B2 | 12/2003 | Rhad et al. |
| 6,709,419 | B2 | 3/2004 | Woehr |
| 2005/0015053 | A1 | 1/2005 | Parker |
| 2007/0038188 | A1 | 2/2007 | Bialecki et al. |
| 2007/0270754 | A1 | 11/2007 | Soderholm et al. |

FOREIGN PATENT DOCUMENTS

| DE | 20 315 872 U1 | 2/2004 |
| WO | 0123029 A1 | 4/2001 |
| WO | WO 0123029 A1 * | 4/2001 |
| WO | 2005079891 A1 | 9/2005 |
| WO | WO 2005/079891 * | 9/2005 |
| WO | WO 2005079891 A1 * | 9/2005 |
| WO | 2008021132 A1 | 2/2008 |

* cited by examiner

*Primary Examiner* — Nicholas Lucchesi
*Assistant Examiner* — Pritesh Patel
(74) *Attorney, Agent, or Firm* — Jeanne Lukasavage; Craig Metcalf; Kirton McConkie

(57) ABSTRACT

A needle shield system may include a needle, an inner tube, a clip within the inner tube, an outer tube, and/or a housing. A method of shielding a needle may include housing a portion of a needle within a clip, housing the clip within an inner tube, housing the inner tube within an outer tube, housing the outer tube within a housing, interlocking the outer tube and the housing, withdrawing the needle from the clip, trapping a tip of the needle between the clip and the inner tube, partially withdrawing the inner tube from the outer tube, and/or releasing the outer tube and the housing from each other.

15 Claims, 9 Drawing Sheets

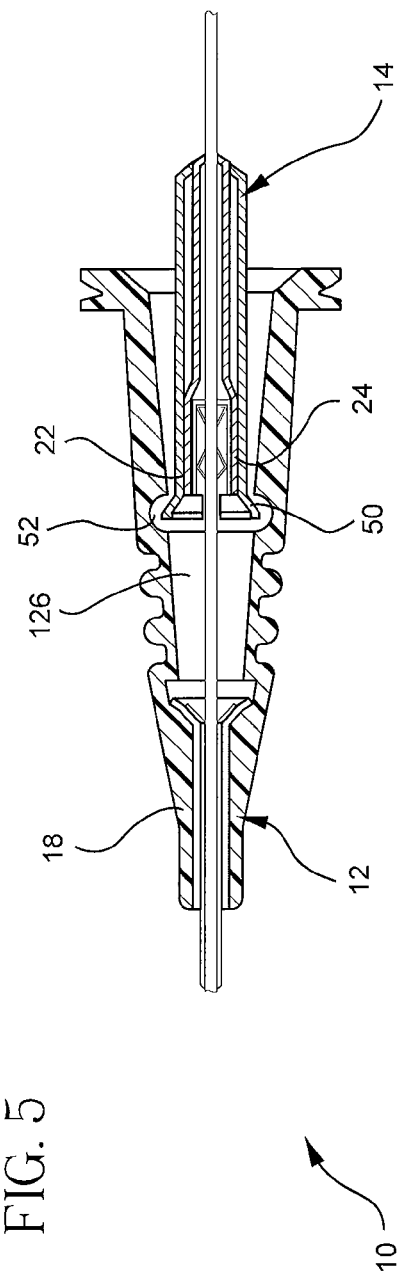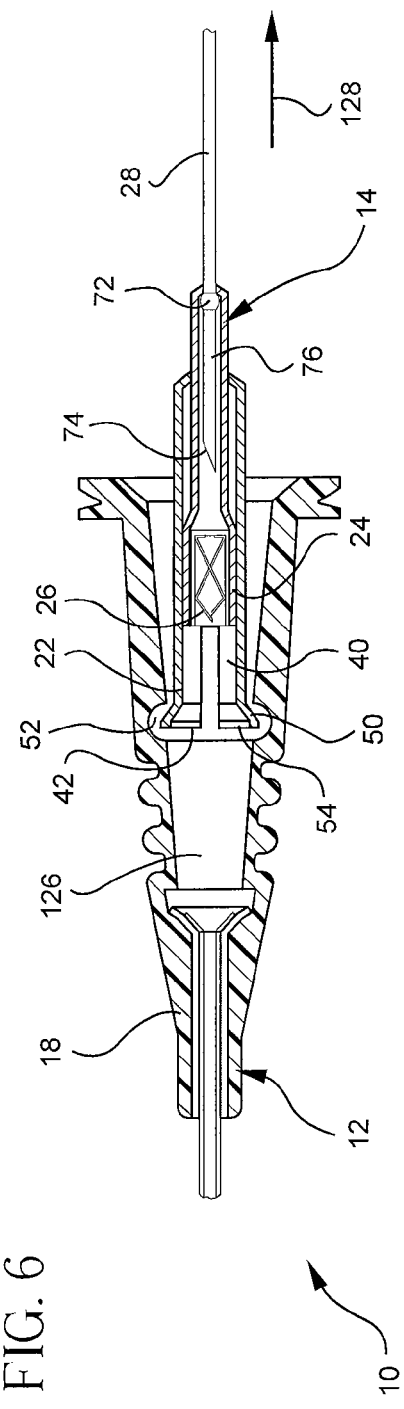

NEEDLE SHIELD AND INTERLOCK

BACKGROUND OF THE INVENTION

This disclosure relates generally to vascular access devices and methods, including hypodermic needles, catheter assemblies, and devices used with catheter assemblies. Generally, vascular access devices are used for communicating fluid with the vascular system of patients. For example, catheters are used for infusing fluid, such as saline solution, various medicaments, and/or total parenteral nutrition, into a patient, withdrawing blood from a patient, and/or monitoring various parameters of the patient's vascular system.

Intravenous (IV) catheter assemblies are among the various types of vascular access devices and over-the-needle peripheral IV catheters are a common IV catheter configuration. As its name implies, an over-the-needle catheter is mounted over an introducer needle having a sharp distal tip. The introducer needle is generally a hypodermic needle coupled to a needle assembly to help guide the needle and to facilitate its cooperation with the catheter. At least the inner surface of the distal portion of the catheter tightly engages the outer surface of the needle to prevent peelback of the catheter and thus facilitate insertion of the catheter into the blood vessel. The catheter and the introducer needle are assembled so that the distal tip of the introducer needle extends beyond the distal tip of the catheter with the bevel of the needle facing up away from the patient's skin. The catheter and introducer needle are generally inserted at a shallow angle through the patient's skin into a blood vessel.

In order to verify proper placement of the needle and/or catheter in the blood vessel, the clinician generally confirms that there is "flashback" of blood in a flashback chamber, which is generally associated with a needle assembly. Once proper placement of the distal tip of the catheter into the blood vessel is confirmed, the clinician may apply pressure to the blood vessel by pressing down on the patient's skin over the blood vessel distal of the introducer needle and the catheter. This finger pressure occludes the vessel, minimizing further blood flow through the introducer needle and the catheter.

The clinician may then withdraw the introducer needle from the catheter. The introducer needle may be withdrawn into a needle tip shield or needle shield that covers the needle tip and prevents accidental needle sticks. In general, a needle tip shield includes a housing, a sleeve, or other similar device that is designed such that when the needle is withdrawn from the patient, the needle tip will be trapped/captured within the needle tip shield. The purpose of the needle tip shield is to house the tip of the needle in a secure location, thereby reducing the possibility of needle sticks when the needle and needle tip shield are separated properly from the catheter, which is left in place to provide intravenous access to the patient.

The separation of the needle assembly from the catheter portions of the catheter assembly presents numerous potential hazards to the clinicians and others in the area. As indicated above, there is a risk of accidental needle sticks if the needle tip is not secured properly in a needle tip shield. Additionally, because the needle has been in contact with blood in the patient's vasculature, blood is often present on the exterior of the needle and is often present inside the lumen of the needle. As the needle is withdrawn, there is a risk that this blood will drip from the needle tip or come into contact with other surfaces to expose clinicians and equipment to blood. Additionally, it has been observed that withdrawing a needle from a catheter assembly often imparts energy to the needle assembly, such as by the intentional or unintentional bending forces applied to the needle during removal. This energy has been observed to cause blood to splatter or spray from the needle as the needle wiggles and shakes with the stored energy once it is free from the catheter assembly. While prior needle assemblies have provided needle tip shields to reduce the occurrence of needle sticks, these prior enclosures and clips have not sufficiently addressed the risk that clinicians and equipment may be exposed to blood from the needle without experiencing a needle stick. While the problem of blood exposure from needle tips used in over-the-needle catheters is a common problem, blood exposure risks are also problematic in other uses of hypodermic needles where the needle tip has been in contact with blood. The present disclosure presents systems and methods to significantly limit and/or prevent such blood exposure.

BRIEF SUMMARY OF THE INVENTION

The systems and methods of the present disclosure have been developed in response to problems and needs in the art that have not yet been finally resolved by currently available vascular access systems and methods. Thus, these systems and methods are developed to provide safer vascular access systems that reduce blood exposure.

A vascular access system may include a needle shielding system. The needle shielding system may include a needle, an inner tube, a clip, an outer tube, and/or a housing. The needle may have a tubular shaft with an outer diameter, a distal end, and a proximal end. The needle may also have a needle tip at the distal end and a feature near the needle tip. The inner tube may have an inner diameter and an outer diameter. The inner diameter of the inner tube may be greater than the outer diameter of the of the needle. The inner tube may also have an outer diameter. The clip may reside or be housed within the inner tube. The outer tube may have an inner diameter and an outer diameter. The inner diameter of the outer tube may be greater than the outer diameter of the inner tube. The housing may also have an inner diameter. The inner diameter may be greater than the outer diameter of the outer tube.

The outer tube of the needle shielding system may also include an outer surface, and the needle shielding system may include an interlock formed on the outer surface of the outer tube. The housing may include an inner surface, and the needle shielding system may include an interlock mate formed on the inner surface of the housing. The outer tube may include a longitudinal axis and at least one slit formed along at least a portion of the outer tube along the longitudinal axis.

The inner tube of the needle shielding system may also include a proximal end and a barrier at the proximal end. The inner tube may include a section capable of housing the needle tip and feature between the clip and the barrier when the feature is adjacent the barrier. The clip may prevent the needle tip from extending distally beyond the clip after the needle tip is withdrawn proximally past the clip. The inner tube may include an outer surface and a tube interlock on the outer surface. The outer tube includes an inner surface and a tube interlock mate on the inner surface.

The feature may be a crimp, ferrule, or similar structure or formation. The outer tube may bias radially inwardly towards the longitudinal axis along the at least one slit. The interlock may include at least one finger that extends radially outwardly from the longitudinal axis.

A method of accessing the vascular system of a patient may include shielding a needle and preventing blood exposure during and after access of the vascular system. The method may include housing a portion of a needle within a clip, housing the clip within an inner tube, housing the inner tube within an outer tube, housing the outer tube within a housing, interlocking the outer tube and the housing, withdrawing the needle from the clip, trapping a tip of the needle between the clip and the inner tube, partially withdrawing the inner tube from the outer tube, and/or releasing the outer tube and the housing from each other. Withdrawing the needle from the clip may include withdrawing the portion of the needle and the needle tip from the clip. The method may also include interlocking the inner tube and the outer tube after partially withdrawing the inner tube from the outer tube and/or closing the clip after withdrawing the needle portion and needle tip from the clip. The needle may include a feature near the needle tip, and the method may include interlocking the feature of the needle and the inner tube. The method may include containing blood within the inner tube.

Various embodiments of a needle shielding system or similar vascular access device within a vascular access system may include means for accessing the vascular system of a patient, means for temporarily housing means for accessing, means for containing means for accessing, means for interlocking with means for housing, and means for supporting means for interlocking. A needle shielding system may include means for shielding means for accessing. A needle shielding system may include means for releasing means for interlocking from means for housing.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein need to be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

FIG. 5 is a cross section view of an example of a needle shield system with an inner tube supporting an outer tube.

FIG. 6 is a cross section view of an example of a needle shield system with an inner tube withdrawing from an outer tube.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
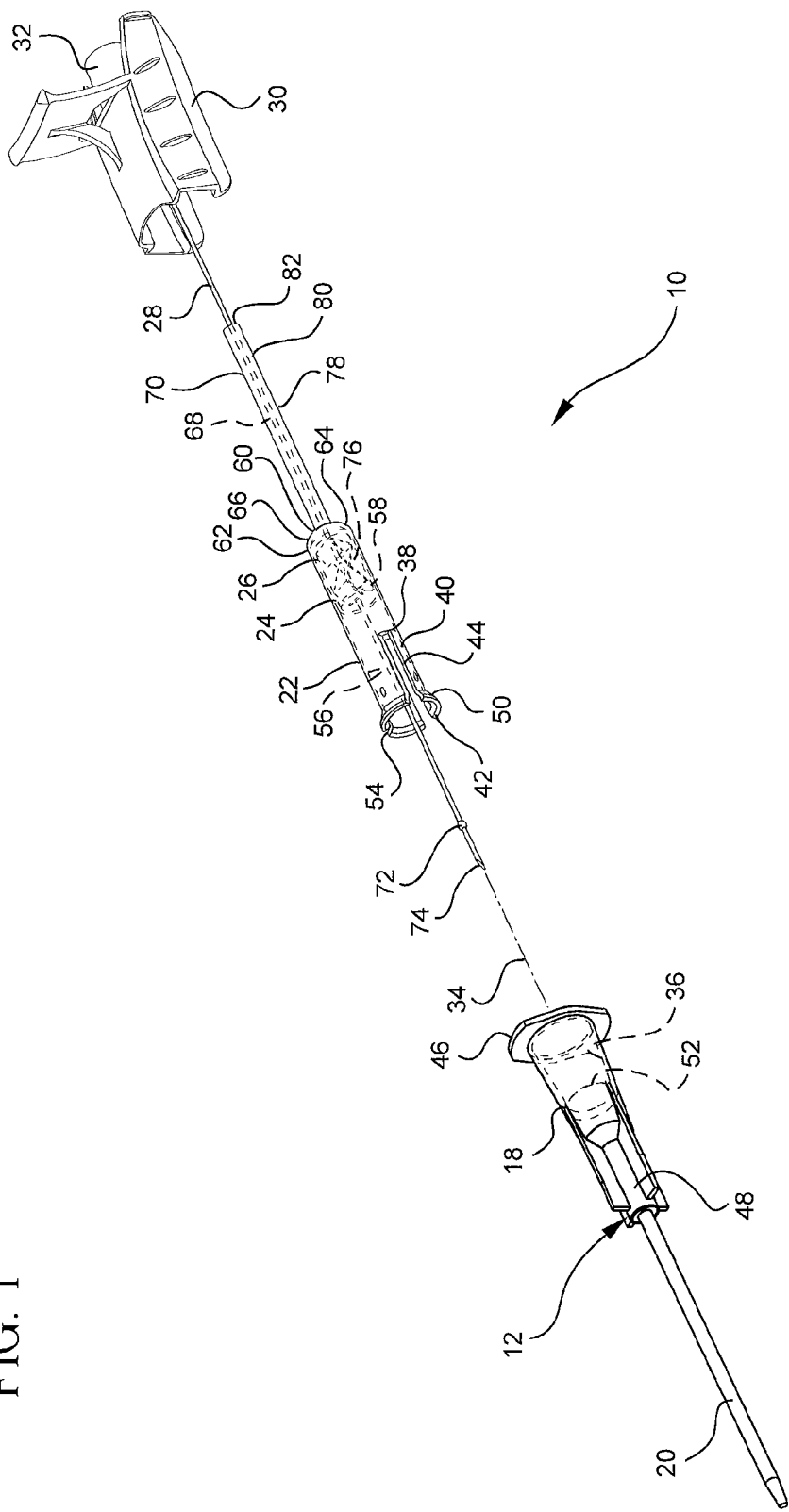
FIG. 1 is a perspective view of an example of a vascular access system.

Referring to FIG. 1, a perspective view shows an example of a vascular access system 10. This example of a vascular access system 10 includes a catheter assembly 12, a needle shield assembly 14, and a needle assembly 16. The catheter assembly 12 includes a catheter adapter housing 18 and a catheter 20. The needle shield assembly 14 includes an outer tube 22, an inner tube 24, and a needle shield, barrier, or clip 26. The needle assembly 16 includes a needle 28, a needle hub 30, and a vent plug 32. The vascular access system 10, and each major component thereof, runs along a longitudinal axis 34.

The housing 18 has an inner diameter 36 slightly larger than an outer diameter 38 of the outer tube 22. The slightly smaller outer diameter 38 of the outer tube 22 permits the outer tube 22 to be inserted into the lumen formed by the inner diameter 36 of the housing 18. As the outer tube 22 is inserted into the housing 18, at least one finger 40 formed at a distal end 42 of the outer tube 22 by at least one slit 44 compresses radially inwardly towards the longitudinal axis 34 to permit the outer tube 22 to fit within the housing 18. The at least one slit 44 is formed along at least a distal portion of the outer tube 22, along or parallel with the longitudinal axis of the outer tube 22. Thus, the finger 40 can be compressed inwardly in order for the outer tube 22 to be inserted within the inner diameter 36.

The outer tube 22 may be advanced from a proximal end 46 of the housing 18 towards a distal end 48 of the housing 18 until an interlock 50 on the outer surface of the outer tube 22 engages with an interlock mate 52 on the inner surface of the housing 18. The interlock 50 and interlock mate 52 may be any combination of interlocking structures. The interlock 50 of the example shown in FIG. 1 is formed of multiple annular end flanges 54 extending radially outward from the longitudinal axis 34 and the distal ends of the multiple fingers 40. The interlock mate 52 is a recessed ring formed on the inner surface of the housing 18.

The outer tube 22 includes an inner diameter 56 slightly larger than an outer diameter 58 of the inner tube 24. The slightly smaller outer diameter 58 of the inner tube 24 permits the inner tube 24 to be inserted into the lumen formed by the inner diameter 56 of the outer tube 22. As the inner tube 24 is advanced from a proximal end 60 of the outer tube 22 towards the distal end 42 of the outer tube 22, the outer surface of the inner tube 24 comes into proximity and/or contact with the fingers 40 and/or interlock 50. When the inner tube 24 is fully advanced towards the distal end 42 of the outer tube 22, the outer surface of the inner tube 24 forms a support for the fingers 40 and/or interlock 50. During support by the inner tube 24, the interlock 50 may not disengage from the interlock mate 52. The slightly smaller outer diameter 58 of the inner tube 24 prevents the slightly larger inner diameter 58 of the outer tube 22 from decreasing to the degree needed to move the interlock 50 in a radially inward direction towards the longitudinal axis 34 and to a degree sufficient to release the interlock 50 from the interlock mate 52.

The inner tube 24 may also be retracted or withdrawn through the lumen of the outer tube 22. The fingers 40 or structures near the distal end 42 of the outer tube 22 may be manufactured, that is, bent, creased, folded, molded, or otherwise formed, to bias radially inwards towards the longitudinal axis 34. When the inner tube 24 is withdrawn in a proximal direction from the biased section of the distal end 42 of the outer tube, the fingers 40 may move in a radially inward direction, disengaging the interlock 50 from the interlock mate 52. This is facilitated by the fact that the fingers 40 may flex inwardly. The junction formed between the biased distal end 42 of the outer tube 22 and the outer surface of the distal end of the inner tube 24 will be of sufficient strength to withstand movement under the withdrawal force caused as the needle 28 is withdrawn through the needle shield assembly 10 and clip 26.

The inner tube 24 includes a tube interlock 62 on the outer surface of a middle section 64 of the inner tube 24. The tube interlock 62 is formed as a surface that tapers radially inward towards the longitudinal axis 34 as the surface moves from the distal end of the inner tube 24 towards the proximal end of the inner tube 24. A corresponding tube interlock mate 66 is formed on the inner surface of the outer tube 22 at the proximal end 60 of the outer tube 22. The tube interlock mate 66 is a surface or edge that tapers or is formed to extend radially inward towards the longitudinal axis 34 of the outer tube 22. At one point, the tube interlock mate 66 includes a smaller inner diameter than the outer diameter of the tube interlock 62. Thus, the tube interlock 62 may not be retracted or withdrawn beyond the tube interlock mate 66 and the proximal end 60 of the outer tube 22. The outer tube 22 may also include an additional tube interlock mate on the inner surface of the distal end 42 of the outer tube 22 to prevent the distal end of the inner tube 24 from advancing beyond the distal tube interlock mate and the distal end 42 of the outer tube 22.

The inner tube 24 includes an inner diameter 68 slightly larger than an outer diameter 70 of the tubular shaft of the needle 28. The slightly smaller outer diameter 70 of the needle 28 permits the needle 28 to be inserted into the lumen formed by the inner diameter 68 of the inner tube 24. As the needle 28 retreats or is withdrawn through the inner tube 24, a feature 72 on the needle 28 and a nearby tip 74 of the needle 28 is pulled through the clip 26. The inner tube 24 houses the clip 26 within a large chamber 76 of the inner tube 24. The clip 26 is lodged in a fixed position within the large chamber 76 such that the clip 26 will not move from the large chamber 76 when placed under the force caused by movement of the needle 28 and feature 72 through the clip 26.

After the feature 72 and needle tip 74 are withdrawn from the clip 26 in a proximal direction, the feature 72 and needle tip 74 are housed within a section or small chamber 78 of the inner tube 24. As the needle 28 is withdrawn further towards a proximal end 80 of the inner tube 24, the feature 72 ultimately comes into contact with a barrier 82 at the proximal end 80 of the inner tube 24. The barrier 82 may be any structure capable of halting the progression of a feature 72. For example, where the feature 72 is a crimp or a ferrule, the feature barrier 82 may be a collar of material having a slightly smaller inner dimension than the outer dimension of the crimp or ferrule. Thus, the crimp or ferrule will be unable to pass through the collar.

Further, after the needle tip 74 is withdrawn proximally past the clip 26, the clip 26 engages or closes in a manner that prevents the needle tip 74 from reentering the clip 26 and advancing in a distal direction. Thus, after the feature 72 and needle tip 74 are fully withdrawn proximally beyond the clip 26 and into the small chamber 78 of the inner tube 24, the feature 72 and needle tip 74 are effectively and safely locked between the clip 26 and the barrier 82. With the needle tip 74 safely locked within the small chamber 78, an operator of the vascular access system 10 may safely remove the needle 28 from a patient without risking being stuck by the needle tip 74 and thus contaminating the operator's vascular system with the blood of a patient.

The telescoping nature of the needle shield assembly 14 also provides multiple barriers and containers to prevent blood from spilling or exiting the needle shield assembly 14 after the needle tip 74 is locked and the assembly 14 is disengaged from the catheter assembly 12. For example, blood exuding from the needle tip 74 when the needle tip 74 is locked within the small chamber 78 will be retained within the small chamber 78 under surface tension of the inner surface of the small chamber 78. Similarly, blood located within the large chamber 76 will be retained within the large chamber 76 under the surface tension and barrier of both the inner surface of the large chamber 76 and the multiple surfaces of the clip 26. Blood located just distal to the distal most end of the inner tube 24 and within the outer tube 22 will be retained within the outer tube 22 under the surface tension of the inner surface of the outer tube 22. The overall structure of the telescope formed by the needle shield assembly 14 provides a continuous, and relatively long, chamber capable of housing blood and preventing blood from escaping from the distal end of the needle shield assembly 14 during removal of the needle shield assembly. By preventing the loss of blood from the inner portion of the needle shield assembly 14, an operator will be able to remove the needle 28 and needle shield assembly 14 from the vascular access system 10 with minimal blood exposure risk to the operator.

In the example of a vascular access system 10 described with reference to FIG. 1, the needle assembly 16 includes a needle hub 30. The needle hub 30 provides a tactile feature that an operator may use to advance, retract, and manipulate the location and orientation of the needle 28 and system 10. The needle 28 is secured to the needle hub 30. Any other vascular access device may be secured in series or parallel to the needle hub 30. For example, the vent plug 32 secured to the proximal end of the needle hub 30 provides a vent through which air may pass while blood advances from a patient's vascular system, into the needle tip 74, and proximally along the length of the needle 28. When the blood comes into contact with certain vent plugs 32, the vent plug 32 will become plugged and allow no further air or blood to pass through the vent plug 32.

Figure 2:
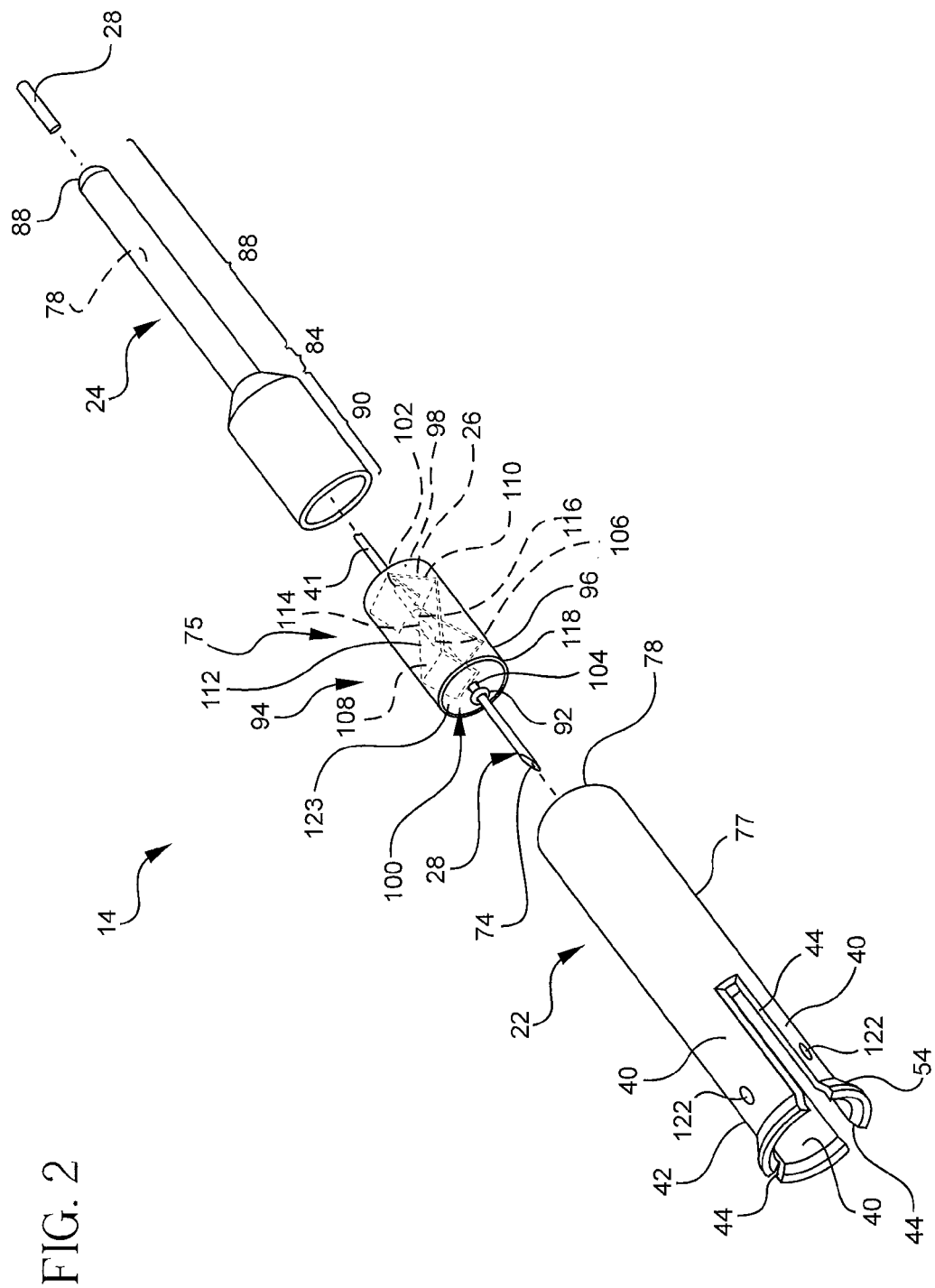
FIG. 2 is an exploded perspective view of an example of a needle shield system.

Referring to FIG. 2, an exploded perspective view of an example of a needle shield assembly 14 and an example of a needle 28 shows components of the needle shield assembly 14 including the outer tube 22, the inner tube 24, and a needle point barrier 84 including a clip 26. The outer tube 22 includes a tubular body 86 with a proximal end 60 that is radially inwardly tapered to closely and slidably engage with the inner tube 24. The outer tube 22 also includes multiple annular end flanges 54 at a distal end 42 that extend radially outwardly and are adapted to engage the interlock mate 52 of housing 18 (FIG. 1). A plurality of flexible interlock fingers 40 (three in this example) are formed by a plurality of longitudinal grooves or slits 44 that extend proximally and radially inward from the end flanges 54. The fingers 40 flex inwardly to permit the end flanges 54 to fit within the lumen of housing 18 to engage the interlock mate 52. The end flanges 54 include a "ramped" or triangular radial cross section to mate with the interlock mate 52 of housing 18. The "ramped" mating between the end flanges 54 and the interlock mate 52 allows manual application of a moderate proximally-directed force to inwardly flex the fingers 40 to disengage the outer tube 22 from the housing 18.

The inner tube 24 includes a proximal section 88 of smaller diameter and a distal section 90 of larger diameter interconnected by an annularly tapered middle section 64. The distal section 90 closely and slidably fits within the body 86 of the outer tube 22. A proximal end 80 of the inner tube 24 is radially inwardly tapered to closely and slidably engage the body of the needle 28 but not let the ferrule 92 pass.

In the example of a needle shield assembly 14 described with reference to FIG. 2, the needle point barrier 84 includes a tubular housing 94 that contains a protective device in the form of a safety clip 26. The housing 94 includes a tubular body 96 that closely fits within the distal section 90 of the inner tube 24. Respective proximal and distal end disks 98 and 100 affixed to the body 96 have respective needle holes 102 and 104 of sufficient size to pass the body and the ferrule 92 of the needle 28 through the needle holes 102 and 104. The safety clip 26 has a pair of arms 106 and 108 interconnected by a base leg 110 and is stamped and formed from stainless steel or other suitable resilient, non-corroding metal or plated metal, or molded from a suitable plastic material. The safety clip 26 is biased to close over the needle tip 74 where the arms 106 and 108 are bent under tension and are relaxed after the safety clip 26 has closed over the needle tip 74. The arm 106 is narrowed to pass through a rectangular slot 112 of the arm 108. The needle 28 passes through an oval hole 114 of the arm 106, through the slot 112 of the arm 108, and through a hole 116 of the base leg 110. Each of the slot 112, hole 114, and hole 116 are of sufficient size to pass the body and the ferrule 92 of the needle 28 through the slot 112, hole 114, and hole 116. The needle 28 is pinched between respective jaws 118 and 120 of the arms 106 and 108 allowing inward movement thereof until the needle tip 74 is withdrawn to a position proximal of the jaws 118 and 120. The jaws 118 and 120 then close together preventing distal movement of the needle tip 74 beyond the clip 26.

The needle point barrier 84 may be permanently affixed within the distal section 90 of the inner tube 24, such as by crimping, press-fitting, or adhesively securing. When affixed in the distal section 90, the proximal end of the needle point barrier 84 forms the distal end of the small chamber 78. The small chamber 78 functions as a tip-receiving chamber of a length slightly larger than the distance from the proximal end of the ferrule 92 to the needle tip 74 to receive the needle tip 74 and ferrule 92 therein. The outer tube 22 may be temporarily secured to the inner tube 24 by a friction fit using a pair of oppositely disposed detents 122 until the safety clip 26 is used.

Figure 3:
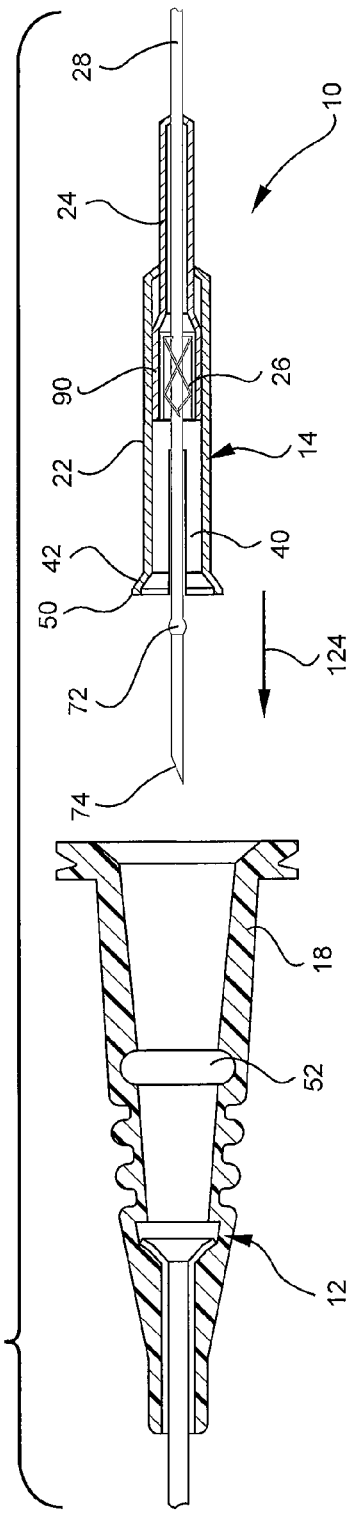
FIG. 3 is a cross section view of an example of a needle shield system with a needle shield assembly approaching an example of a catheter assembly.

Referring to FIG. 3, a cross section view of an example of a needle shield assembly 14 and an example of a catheter assembly 12 shows the needle shield assembly 14 and an example of a needle 28 approaching the catheter assembly 12 in a distal direction 124. During initial assembly of a vascular access system 10, the needle 28 should be fully inserted into the needle shield assembly 14 such that the needle tip 74 and feature 72 are located distal to the clip 26. The needle shield assembly 14 should approach the catheter assembly with the distal section 90 of the inner tube 24 in a position within the outer tube 22 other than at the distal end 42 of the outer tube 22. When the distal section 90 is not located directly adjacent the fingers 40 at the distal end 42 of the outer tube 22, the fingers 40 will be permitted to bias, or at least flex, radially inward towards the longitudinal axis 34 (FIG. 1). When the fingers 40 are permitted to bias, or at least flex, radially inward, the distal end 42 and interlock 50 of the outer tube 22 can easily slide through the lumen 126 of the housing 18 and into the corresponding interlock mate 52.

Figure 4:
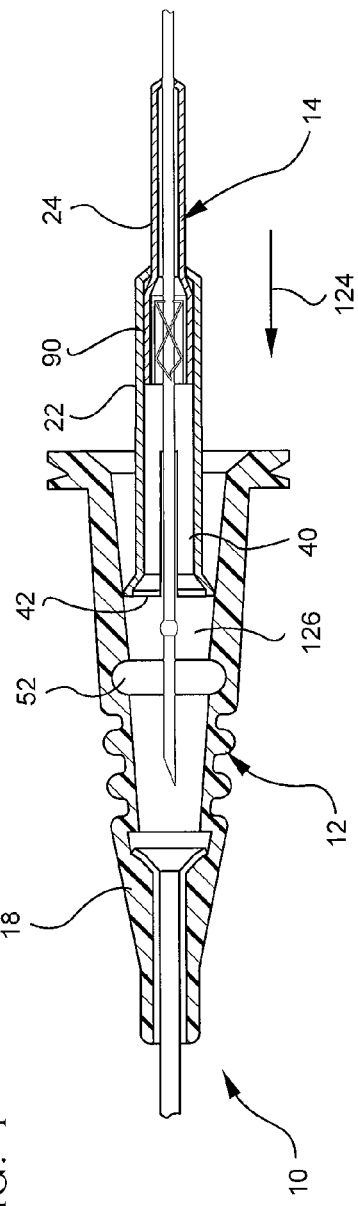
FIG. 4 is a cross section view of an example of a needle shield system with an outer tube engaging with an example of a catheter assembly.

Referring to FIG. 4, a cross section view of an example of a needle shield assembly 14 is shown advanced in a distal direction 124 and at least partially inserted into an example of a catheter assembly 12. During initial assembly of a vascular access system 10, and after the initial advance of the needle shield assembly 14 towards the catheter assembly 12 as shown and described with reference to FIG. 3, the needle shield assembly 14 can be further inserted into the lumen 126 of the housing 18 of the catheter assembly 12. With the distal section 90 still located in a position within the inner tube 24 away from the distal end 42 of the inner tube 24, the fingers 40 are able to bias or flex inward such that the distal end 42 of the outer tube 22 is able to be inserted through the lumen 126 and towards the interlock mate 52.

Referring to FIG. 5, a cross section view of an example of the needle shield assembly 14 is shown fully advanced and inserted into the lumen 126 of an example of a catheter assembly 12. The needle shield assembly 14 is fully inserted into the lumen 126 of the housing 18 of the catheter assembly 12 when the interlock 50 of the outer tube 22 is fully engaged and residing within the interlock mate 52. The inner tube 24 is also advanced towards the distal end 42 of the outer tube 22 such that the inner tube 24 is providing a support to the fingers 40 of the distal end 42 of the outer tube 22 are held between the outer surface of the inner tube 24 and the inner surface of the housing 18. The multiple annular end flanges 54 of the interlock 50 are likewise held in place within the recess of the interlock mate 52. With the interlock 50 and interlock mate 52 engaged and locked together, the remainder of the needle shield assembly 14 is engaged and locked to the housing 18 of the catheter assembly 12.

Referring to FIG. 6, a cross section view of an example of the needle shield assembly 14 is shown partially withdrawn from an example of a catheter assembly 12. During withdrawal of the needle shield assembly 14 from the catheter assembly 12, the needle 28 is first pulled or withdrawn in a proximal direction from the vascular system of a patient, through the catheter 20, through the catheter housing 18, through the distal end 42 of the outer tube 22, through the distal end of the inner tube 24, through the clip 26, and into the small chamber 76 of the inner tube 24 in a distal direction 128. The inner tube 24 supports the fingers of the outer tube 22 until they are allowed to collapse by the rearward movement of the inner tube 24. When the feature 72 and tip 74 of the needle 28 are distally withdrawn from the clip 26 such that the clip 26 locks, the feature 72 comes into contact with the barrier 82. The distal force from the withdrawing needle 28 is then transferred from the feature 72 to the barrier 82, which in turn forces the inner tube 24 in the distal direction 128. As the inner tube 24 moves in the distal direction 128, the distal section 90 of the inner tube 24 moves away from the interlock 50 and fingers 40, permitting the multiple annual end flanges 54 of the interlock 50 to begin to release from the recess of the interlock mate 52. The inner tube supports the fingers of the outer tube until they are separated and the fingers are allowed to collapse inwardly. The flanges 54 either release as a result of a preformed bias of the fingers 40 towards a radially inward direction or as a result of the "ramped" interface between the interlock 50 and the interlock mate 52 surfaces, which cause the fingers 40 to move radially inward as a distal force is applied to the outer tube 22.

Figure 7:
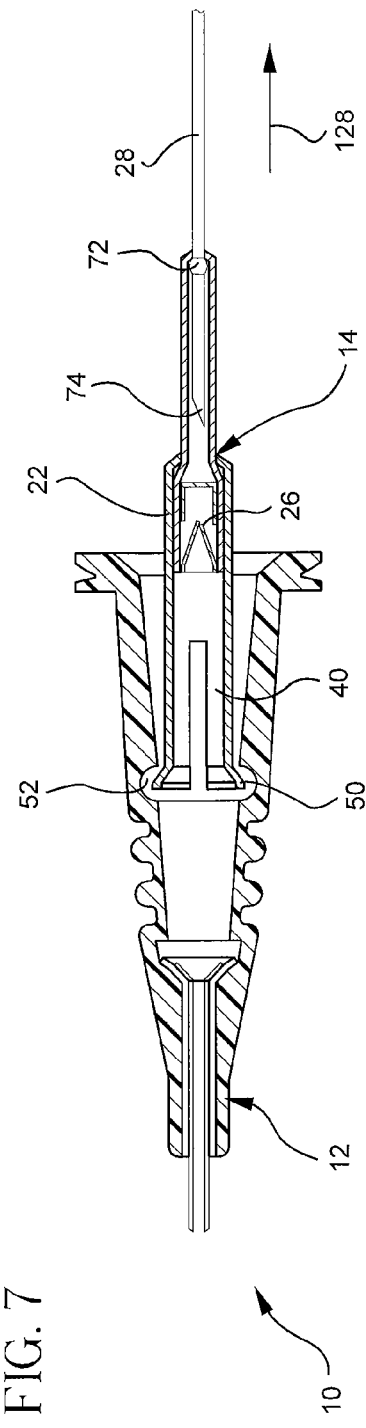
FIG. 7 is a cross section view of an example of a needle shield system with an outer tube releasing from the housing of an example of a catheter assembly.

Referring to FIG. 7, a cross section view of an example of the needle shield assembly 14 is shown further withdrawn from an example of a catheter assembly 12. During further withdrawal of the needle shield assembly 14 from the catheter assembly 12, the feature 72 and tip 74 of the needle 28 remain trapped within the small chamber 76 of the inner tube. The distal section 90 of the inner tube 24 is at the proximal end 60 of the outer tube 22, and the tube interlock 62 of the inner tube 24 is fully engaged with the tube interlock mate 66 of the outer tube. As distal force is applied to the needle 28 and inner tube 24, the tube interlock 62 transfers the distal force to the corresponding tube interlock mate 66, forcing the outer tube 22 in a distal direction 128. As the outer tube 22 is forced in a distal direction 128, the "ramped" interface between the interlock 50 and the interlock mate 52 surfaces causes the fingers 40 to move radially inward, thus separating the interlock 50 from the interlock mate 52.

Figure 8:
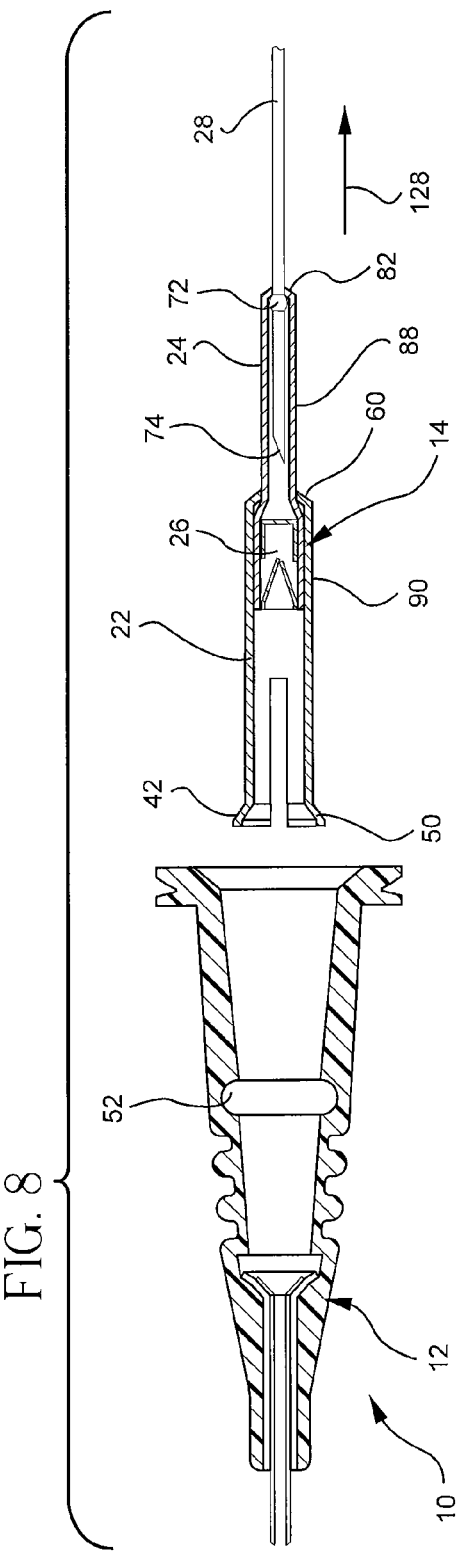
FIG. 8 is a cross section view of an example of a needle shield system with a needle shield assembly withdrawn from an example of a catheter assembly.

Referring to FIG. 8, a cross section view of an example of the needle shield assembly 14 is shown fully withdrawn from an example of a catheter assembly 12. After full withdrawal or disengagement of the needle shield assembly 14 from the catheter assembly, the needle shield assembly 14 has been moved in a distal direction 128. Further, the feature 72 and tip 74 of the needle 28 are trapped and locked within the small chamber 76 of the proximal section 88 of the inner tube 24 between the barrier 82 and the clip 26. The distal section 90 of the inner tube 24 is at the proximal end 60 of the outer tube 22. And, the distal end 42 of the outer tube is fully removed from the lumen 126 of the housing 18.

Figure 9:
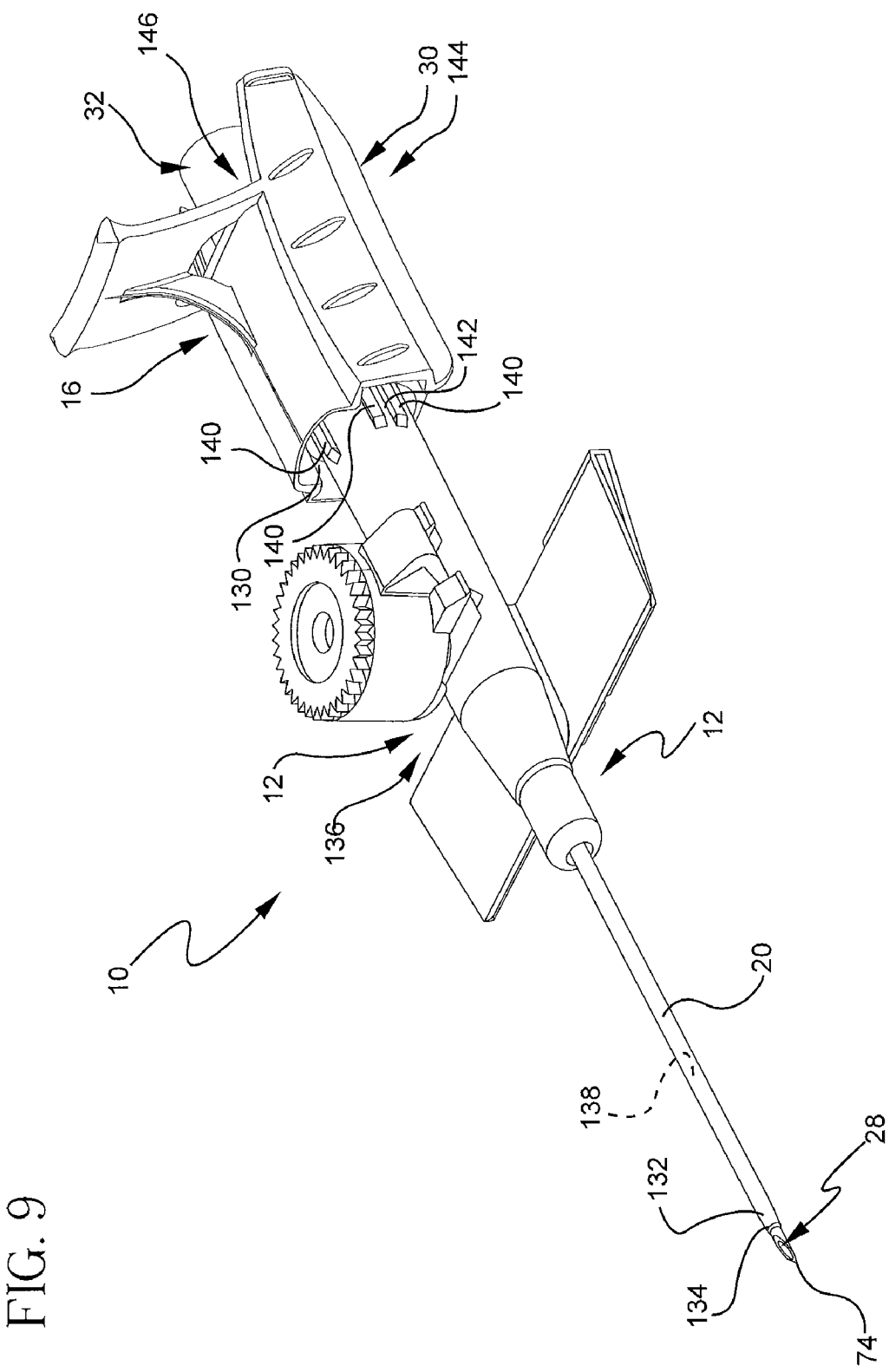
FIG. 9 is a perspective view of an example of a vascular access system.

Referring to FIG. 9, a perspective view of an example of a vascular access system 10 is shown. In this example, the vascular access system 10 includes a catheter assembly 12 and a needle assembly 16. The catheter assembly 12 has a proximal end 130 and a distal end 132 and includes a catheter 20 having an opening 134 at the distal end 132 of the catheter assembly 12 and a catheter hub 136 disposed at the proximal end 130 of the catheter assembly 12. The catheter assembly 12 also defines a lumen 138 extending from the proximal end 130 to the distal end 132.

The needle assembly 16 includes a hypodermic needle 28 having a tubular shaft or body that extends through the lumen 138 of the catheter assembly 12. The needle 28 has a crimp or other feature such as a radial feature or a ferrule affixed to the body at a fixed distance adjacent a needle tip 74. The needle tip 74 extends through the opening 134 of the catheter 20 with the ferrule disposed within the catheter 20.

While the needle assembly 16 is configured for use with the catheter assembly 12, other needle assemblies within the scope of the present disclosure may include hypodermic needles (not shown) adapted for other applications. For example, the needle assembly 16 may or may not include the needle hub 30 of the configuration illustrated. As another example, the needle shield assembly 14 and/or needle assembly 16 may not be attached to a catheter assembly 12. Rather, the needle shield assembly 14 and/or needle assembly 16 may be attached to any vascular access device, such as a device having a septum or valve, including a closed Luer access adapter. Additional details regarding the needle assembly 16 and sub-components thereof will be described below.

Figure 10:
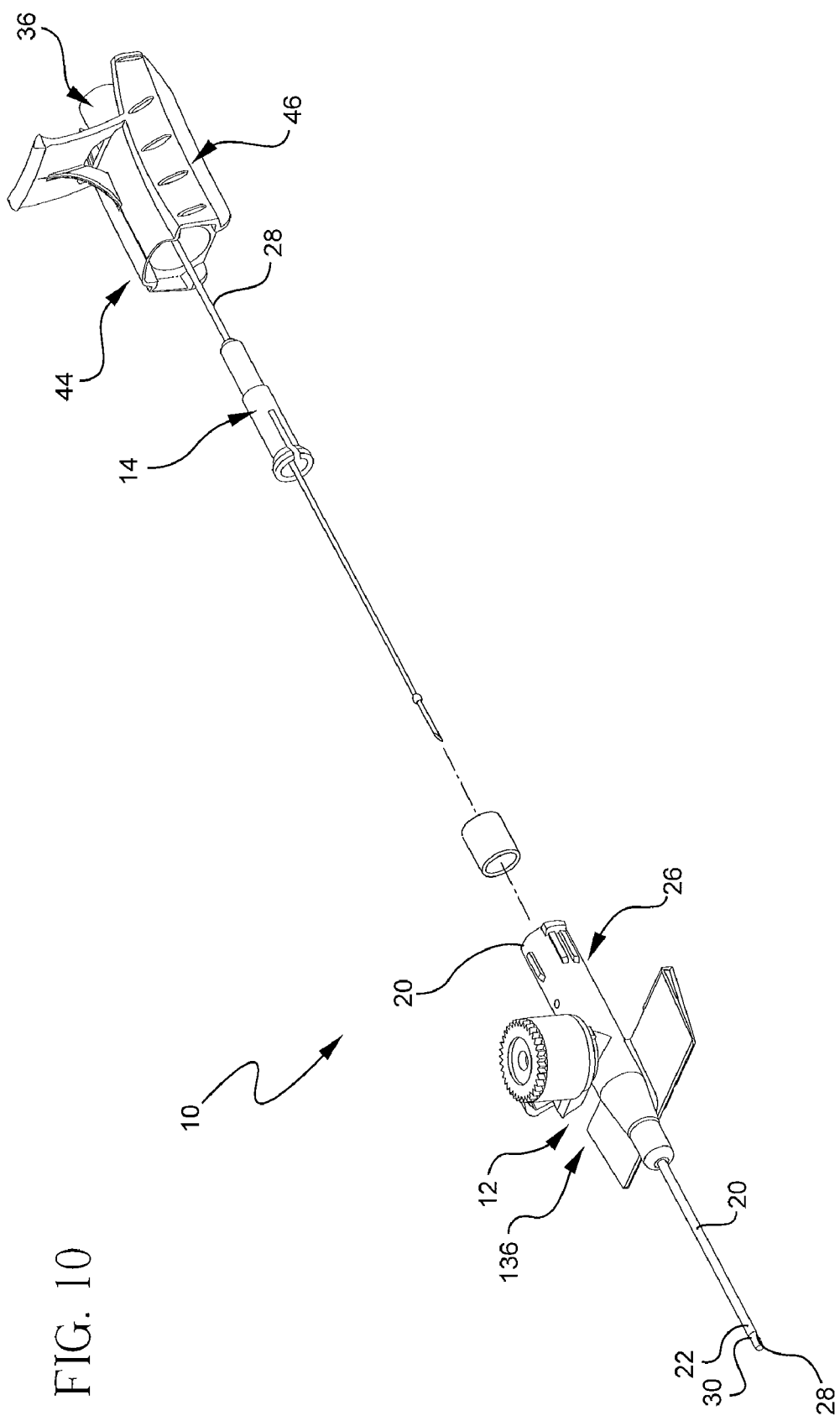
FIG. 10 is an exploded view of the vascular access system of FIG. 9.

Referring to FIG. 10, an exploded view of a vascular access system 10 similar to that shown in FIG. 9 shows the needle 28 withdrawn from the catheter 20. FIG. 10 illustrates the needle shield assembly 14 and the attached needle 28 having been withdrawn from the catheter assembly 12.

Figure 11:
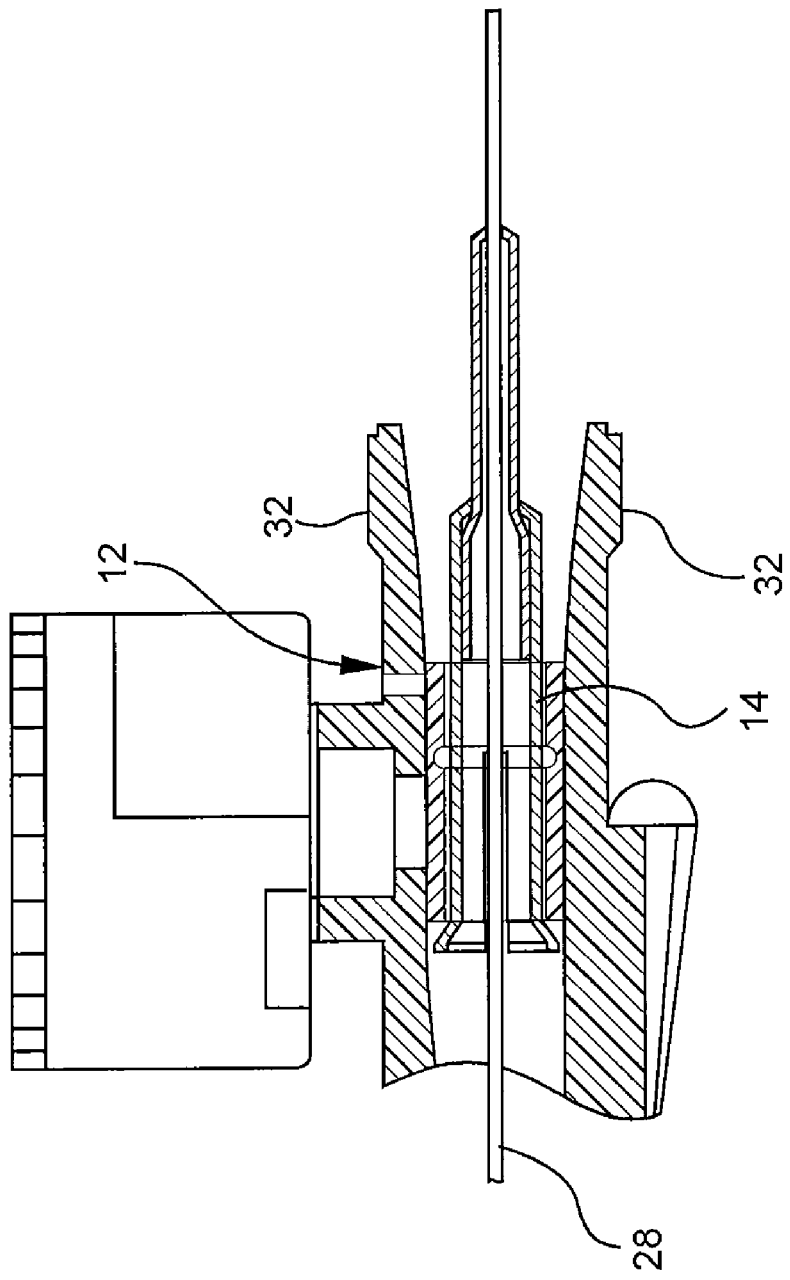
FIG. 11 is a cross section view of a portion of the catheter adapter of FIG. 10 showing the needle shield assembly secured in a place.

FIG. 11 is a cross section view of the interior of the catheter assembly 12. FIG. 11 illustrates the manner in which the needle 28 and needle shield assembly 14 are seated together prior to operation.

Figure 12:
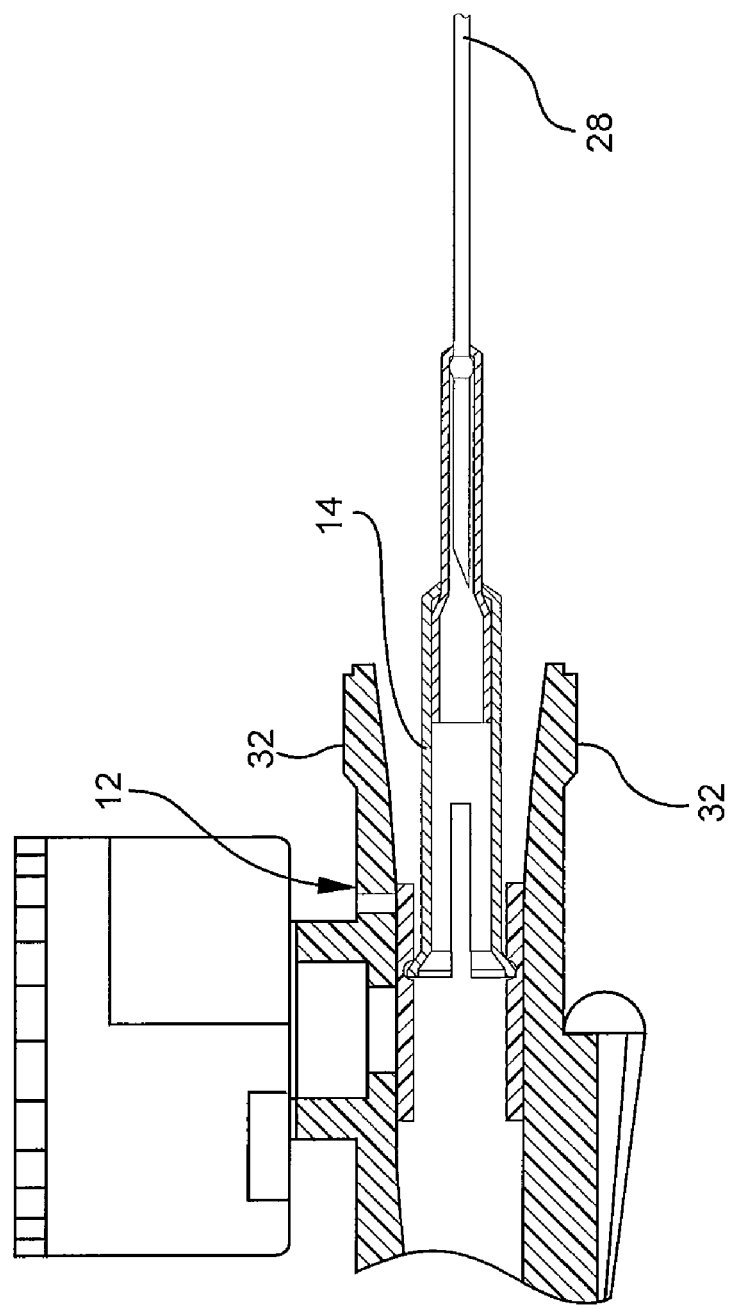
FIG. 12 is a cross section view of a portion of the needle shield assembly of FIG. 10 showing the needle partially withdrawn.

FIG. 12 is a cross section view illustrating the needle shield assembly 14 being withdrawn from the catheter assembly 12.

Various modifications to the needle shield assemblies of the present invention are possible while staying within the same inventive concept. For example, the needle shield assemblies can be used to protect the tip of a cannula in an IV catheter, a stylet in a long anesthesia needle, a catheter adapter, and other such medical devices. The cross section of the needle shield assembly and/or tubular housing can be of other shapes such as square, rectangular, triangular, oval, polygonal, and the like. The feature of the needle can be non-symmetrical and formed other than by crimping the shaft or affixing a ferrule. The radial feature can be retained to prevent proximal movement beyond the inner tube by means other than the radially inward taper. Likewise, the outer tube can slidably engage the inner tube by means other than the radially inward taper of the tube interlock and tube interlock mate. A needle barrier, safety clip, and barrier of a different design may be used to retain the needle tip and/or feature within the small chamber. Any structure may be used to provide an interlock and interlock mate. Further, any element of any embodiment described above may be combined in any number or orientation with any other element of any embodiment.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:
1. A needle shielding system, comprising:
   a needle having a needle feature near a tip of the needle;
   a needle shield having an inner tube at least partially disposed within and telescoping within an outer tube of the needle shield, the needle extending through, and telescopically moveable through, the inner tube, the inner tube having a barrier on a proximal end of inner tube, the barrier being shaped and sized to prevent the needle feature from being drawn proximally through the barrier, wherein the outer tube includes an outer surface and further comprising an interlock formed on the outer surface of the outer tube, wherein the outer tube includes a longitudinal axis and at least one slit formed along at least a portion of the outer tube along the longitudinal axis;
   a catheter housing selectively receiving the needle shield within an inner lumen of the catheter housing, wherein the catheter housing includes an inner surface and further comprising an interlock mate formed on the inner surface of the housing, the interlock mate being shaped and sized to selectively mate with the interlock of the outer tube.

2. The system of claim 1, wherein the inner tube includes a section capable of housing a needle tip and a needle feature between a clip and the barrier when the feature is adjacent the barrier.

3. The system of claim 2, wherein the clip prevents the needle tip from extending distally beyond the clip after the needle tip is withdrawn proximally past the clip.

4. The system of claim 3, wherein the inner tube includes an outer surface and a tube interlock on the outer surface.

5. The system of claim 4, wherein the outer tube includes an inner surface and a tube interlock mate on the inner surface, the tube interlock mate being shaped and sized to selectively mate with the tube interlock of the outer surface.

6. The system of claim 5, wherein the needle feature is at least one of a crimp and a ferrule.

7. The system of claim 5, wherein the outer tube biases radially inward towards the longitudinal axis along an at least one slit formed along at least a portion of the outer tube along the longitudinal axis.

8. The system of claim 4, wherein the tube interlock includes at least one finger that extends radially outward from the longitudinal axis.

9. A needle shielding system, comprising:
 a needle having a needle feature near a tip of the needle;
 a needle shield having an inner tube at least partially disposed within and telescoping within an outer tube of the needle shield, the needle extending through, and telescopically movable within, the inner tube, the inner tube having a barrier on a proximal end of inner tube, the barrier being shaped and sized to prevent the needle feature from being drawn proximally through the barrier, a clip disposed within the inner tube shaped and sized to prevent a needle tip of the needle from being advanced distally through the clip after the needle tip is withdrawn proximally past the clip;
 a catheter assembly selectively receiving the needle shield within an inner lumen of the catheter housing.

10. The needle shielding system of claim 9, wherein the catheter assembly includes an inner surface and further comprising an interlock mate formed on the inner surface of the catheter assembly.

11. The needle shielding system of claim 10, wherein the outer tube includes an outer surface and further comprising an interlock formed on the outer surface of the outer tube, the interlock being shaped and sized to selectively mate with the interlock mate of the catheter assembly.

12. A needle tip shield comprising:
 an outer tube;
 an inner tube at least partially disposed within and telescoping within an outer tube of the needle shield;
 a barrier disposed on a proximal end of inner tube shaped and sized to prevent a needle feature of a needle from being drawn proximally through the barrier, the needle being telescopically moveable within the inner tube;
 a clip disposed within the inner tube shaped and sized to prevent a needle tip of the needle from being advanced distally through the clip after the needle tip is withdrawn proximally past the clip.

13. The needle shield of claim 12, further comprising a section within the inner tube shaped and sized for housing a distal tip of the needle and a needle feature between the clip and the barrier.

14. The system of claim 12, wherein the inner tube includes an outer surface and a tube interlock on the outer surface.

15. The system of claim 14, wherein the outer tube includes an inner surface and a tube interlock mate on the inner surface.

* * * * *